(12) United States Patent
Wood et al.

(10) Patent No.: US 10,245,071 B2
(45) Date of Patent: Apr. 2, 2019

(54) SYSTEM FOR ILLUMINATION DURING A CORRIDOR BASED PROCEDURE

(71) Applicants: Michael Frank Gunter Wood, Toronto (CA); Cameron Anthony Piron, Toronto (CA); Murugathas Yuwaraj, Toronto (CA); Joshua Lee Richmond, Toronto (CA)

(72) Inventors: Michael Frank Gunter Wood, Toronto (CA); Cameron Anthony Piron, Toronto (CA); Murugathas Yuwaraj, Toronto (CA); Joshua Lee Richmond, Toronto (CA)

( * ) Notice: Subject to any disclaimer, the term of this patent is extended or adjusted under 35 U.S.C. 154(b) by 170 days.

(21) Appl. No.: 15/515,654

(22) PCT Filed: Dec. 23, 2014

(86) PCT No.: PCT/CA2014/000914
§ 371 (c)(1),
(2) Date: Mar. 30, 2017

(87) PCT Pub. No.: WO2016/101056
PCT Pub. Date: Jun. 30, 2016

(65) Prior Publication Data
US 2018/0085141 A1   Mar. 29, 2018

(51) Int. Cl.
*A61B 1/32* (2006.01)
*A61B 17/34* (2006.01)
(Continued)

(52) U.S. Cl.
CPC ...... *A61B 17/3423* (2013.01); *A61B 17/3421* (2013.01); *A61B 90/30* (2016.02);
(Continued)

(58) Field of Classification Search
CPC combination set(s) only.
See application file for complete search history.

(56) References Cited

U.S. PATENT DOCUMENTS

| 2006/0224045 A1 | 10/2006 | Whipple et al. |
| 2007/0100211 A1* | 5/2007 | Selover ................. A61B 17/02 600/199 |

(Continued)

FOREIGN PATENT DOCUMENTS

| WO | 2006108143 A2 | 10/2006 |
| WO | 2008027448 A2 | 3/2008 |

OTHER PUBLICATIONS

Cyr, Patrick, International Search Report, PCT Application No. PCT/CA2014/000914 dated Sep. 3, 2015.
(Continued)

*Primary Examiner* — Sameh Boles
(74) *Attorney, Agent, or Firm* — Perry + Currier Inc.

(57) ABSTRACT

A system for illumination during a corridor based procedure is provided, comprising: a light source; and, an optical probe comprising: a tube having a distal end, a proximal end and one or more sidewalls there between, the optical probe and the light source arranged so that light from the light source is received by the one or more sidewalls, the one or more sidewalls configured to convey the light to the distal end, the distal end configured to receive the light and illuminate a sample adjacent thereto.

20 Claims, 13 Drawing Sheets

(51) Int. Cl.
*A61B 90/30* (2016.01)
*A61B 17/00* (2006.01)
*A61B 34/20* (2016.01)

(52) U.S. Cl.
CPC ..... *A61B 34/20* (2016.02); *A61B 2017/00907* (2013.01); *A61B 2034/2057* (2016.02); *A61B 2090/309* (2016.02)

(56) References Cited

U.S. PATENT DOCUMENTS

2007/0276191 A1 11/2007 Selover et al.
2008/0228195 A1 9/2008 Von Jako et al.

OTHER PUBLICATIONS

Cyr, Patrick, International Preliminary Report on Patentability, PCT Application No. PCT/CA2014/000914 dated Mar. 20, 2017.

\* cited by examiner

SYSTEM FOR ILLUMINATION DURING A CORRIDOR BASED PROCEDURE

FIELD

The specification relates generally to navigation systems and methods for minimally invasive therapy and image guided medical procedures and specifically to a system for illumination during a corridor based procedure.

BACKGROUND

Probes for optical measurements of tissue are being developed for a wide variety of applications and modalities, all focused on providing clinicians with details regarding the state of tissue to guide diagnosis or treatments. While the low penetration of light into biological tissue (on the order of 2 mm) restricts the use of optical techniques to surface or near surface measurements, the potential for optical probes to be miniaturized opens the possibility for probes to be combined with endoscopic or catheter-based techniques. This allows for optical measurements to be made in a wide variety of hollow organs (esophagus, colon, lung, etc.) and as a part of many minimally invasive surgical techniques. The optical modalities for which probes have been developed include broadband spectroscopy (ultraviolet, visible, near infrared, and short wave infrared), fluorescence, Raman spectroscopy, optical coherence tomography, photoacoustic tomography, coherence anti-Stokes Raman spectroscopy, confocal microscopy, among others.

Port-based or corridor surgery is a minimally invasive surgical technique where a port (generally a cylindrical plastic tube open on both ends) is introduced to access the surgical region of interest. Unlike other minimally invasive techniques, such as laparoscopic techniques, the port diameter is larger than the tool diameter, allowing bi-manual tool manipulation within the port. Hence, the tissue region of interest is accessible through the port. The presence of the tissue region of interest at a depth few centimeters below the skin surface and accessible through a narrow corridor allows for optical probe measurements to be made on regions of interest in close proximity to the tissue (contact probe within the port) and at a standoff distance from the tissue (stand-off probe position outside of the port).

While a wide variety of optical probes have been developed for numerous modalities, specific design aspects to enable and enhance the use of these probes within port-based surgery have not been developed. These include: the size of the probe, sterilization tolerance, signal enhancing mechanisms, integration with surgical tools, position and orientation tracking, and integration with other optical systems. At present the lack of these features hinders and restricts the use and utility of optical probes for port-based surgery.

SUMMARY

The present disclosure is generally related to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Further, illuminating the surgical field for port-based corridor surgeries is difficult as light must be driven down a narrow cylindrical access port resulting in only a fraction of light direction towards the port actually reaching the field. The resulting illumination is non uniform due to reflections off the one or more sidewalls of the port.

An aspect of the present specification provides an optical port system for a corridor based procedure comprising: one or more light sources; and, an optical probe comprising: a tube having a distal end, a proximal end and one or more sidewalls there between, the optical probe and the one or more light sources arranged so that light from the one or more light sources is received by the one or more sidewalls, the one or more sidewalls configured to convey the light to the distal end, the distal end configured to receive the light and illuminate a sample adjacent thereto.

The one or more sidewalls can be substantially cylindrical.

The one or more sidewalls can be further configured to one or more of: mix the light when received therein; homogenize the light when received therein; and integrate the light when received therein.

The one or more sidewalls can comprise an integrated light guide.

The one or more sidewalls can be generally transparent between the distal end and the proximal end.

The one or more light sources can be in optical communication with the proximal end, the proximal end configured to receive the light from the one or more light sources.

The optical port system can further comprise one or more optical fibers configured to convey the light from the one or more light sources to one or more of the proximal end and the one or more sidewalls.

The distal end can comprise one or more of: a lens, a microlens, a mirror, a light focusing device, and a light diffusing device.

The one or more sidewalls can comprise glass.

An external side of the one or more sidewalls can be generally transparent and the one or more light sources is located at the external side of the one or more sidewalls.

An internal side of the one or more sidewalls can be generally transparent and the one or more light sources is located at the internal side of the one or more sidewalls.

One or more of an external side and an internal side of the one or more sidewalls can be generally transparent and the one or more light sources is located at one or more of the external side and the internal side of the one or more sidewalls, the one or more light sources comprising one or more of an electroluminescent material, an electroluminescent sheet, a organic light emitting diode (OLED) matrix, and an OLED sheet.

The optical port system can further comprise a control system, and wherein one or more of an external side and an internal side of the one or more sidewalls can be generally transparent and the one or more light sources is located at one or more of the external side and the internal side of the one or more sidewalls, the one or more light sources comprising an addressable matrix of pixels in communication with the control system. The control system can be in communication with a navigation system configured to track one or more of a position and a pose of at least one surgical instrument used with the optical probe, the control system can be configured to control the addressable matrix of pixels in response to one or more of the position and the pose of the at least one surgical instrument.

One or more of an external side and an internal side of the one or more sidewalls can be generally transparent and the one or more light sources can comprise a flexible light emitting material located at one or more of the external side and the internal side of the one or more sidewalls.

An external side of the one or more sidewalls can be generally transparent and the one or more light sources can be proximal the external side of the one or more sidewalls, the external side comprising one or more optical coatings configured to convey light from the one or more light sources into the one or more sidewalls, and an interior side of the one or more sidewalls configured to reflect the light back into the one or more sidewalls.

The optical port system can further comprise one or more optical coatings on the one or more sidewalls, the optical coatings configured to assist in conveying the light to the distal end.

The optical port system can further comprise: a power source; and an electrical connection between the power source and light source.

The one or more light sources can be configured to emit one or more of: visible light, non-visible light, infrared light and ultraviolet light.

The tube can comprise a port configured to receive at least one surgical instrument at the proximal end through to the distal end, and the distal end is further configured to illuminate an area of the sample with which the surgical instrument is interacting.

The optical port system can further comprise a light collection apparatus configured to collect the light reflected from the sample, and a one or more of optical visualization apparatus and imaging apparatus, configured to communicate with the light collection apparatus to image the sample from the light reflected from the sample, using one or more of visible light, non-visible light, infrared light and ultraviolet light.

BRIEF DESCRIPTIONS OF THE DRAWINGS

For a better understanding of the various implementations described herein and to show more clearly how they may be carried into effect, reference will now be made, by way of example only, to the accompanying drawings in which.

Figure 6:
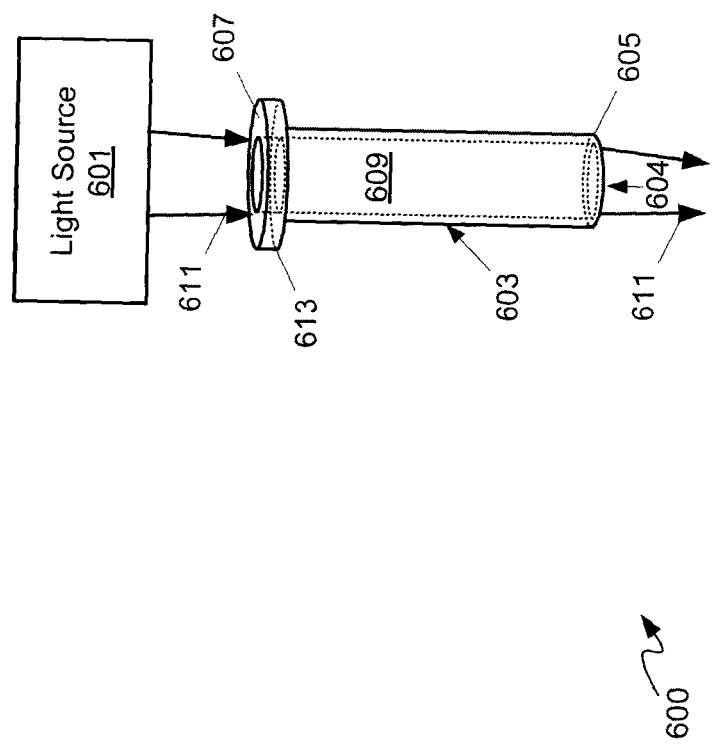
FIG. 6 depicts a system which includes an optical probe that conveys light to sample from a light source using sidewalls of the optical probe, according to non-limiting implementations.
Figure 7:
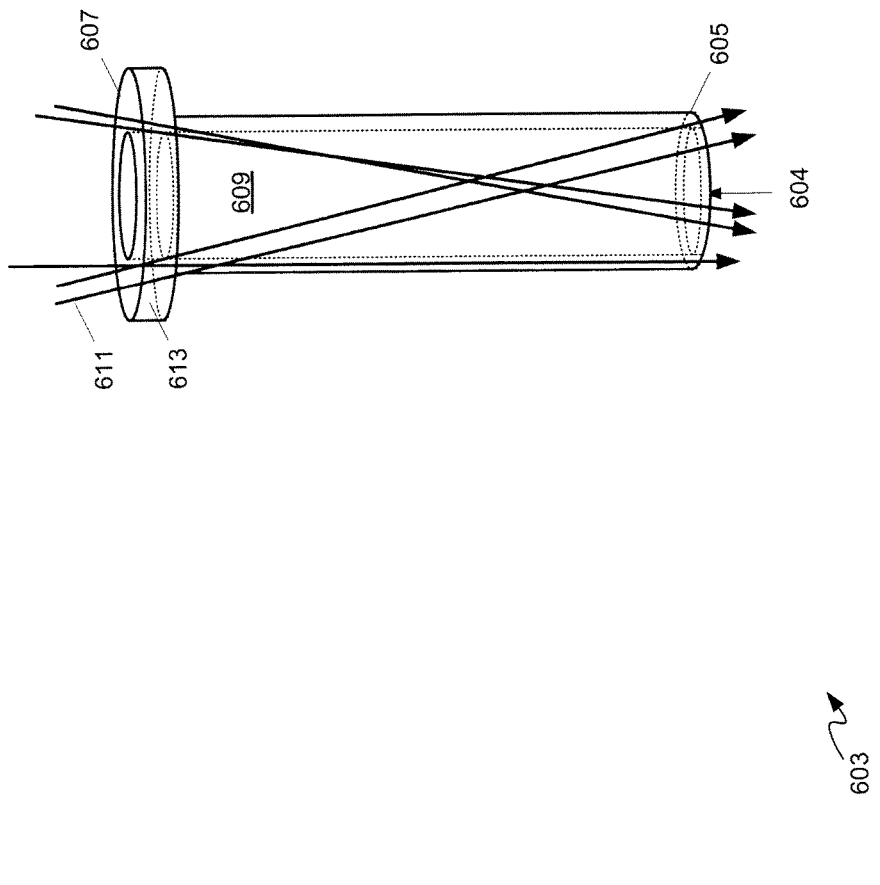

FIG. 7 the optical probe of FIG. 6 in operation, according to non-limiting implementations.

Figure 8:
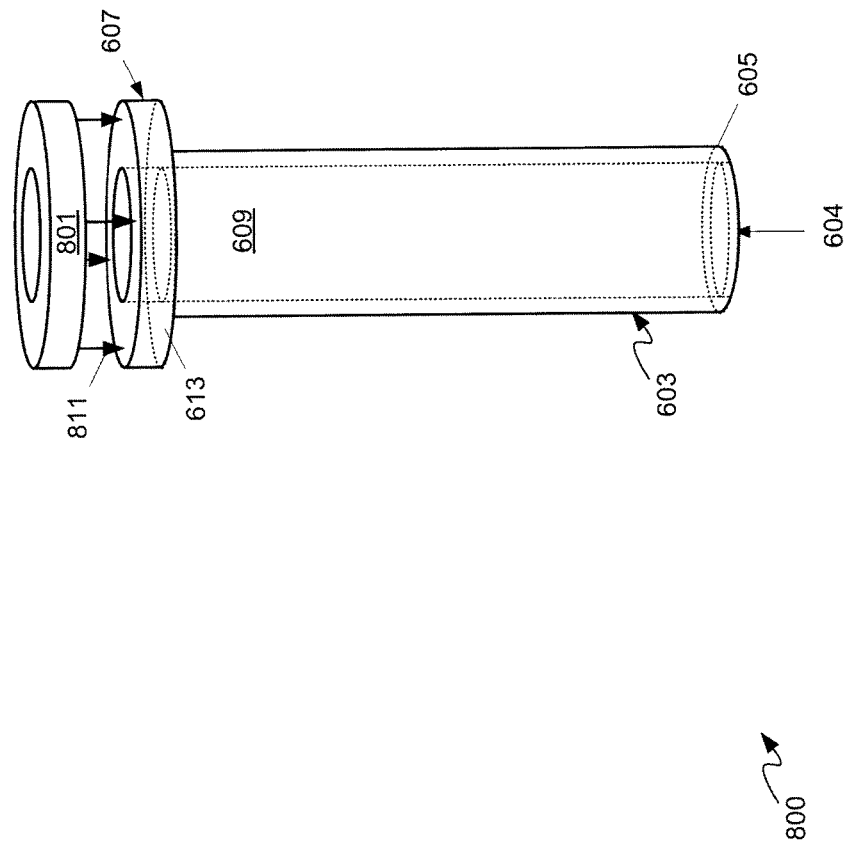

FIG. 8 depicts a system which includes an optical probe that conveys light to sample from a light source using sidewalls of the optical probe, according to alternative non-limiting implementations.

Figure 9:
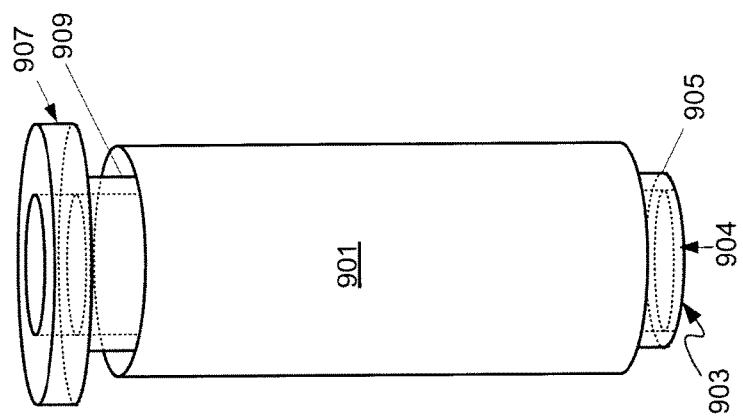

FIG. 9 depicts a system which includes an optical probe that conveys light to sample from a light source using sidewalls of the optical probe, according to alternative non-limiting implementations.

Figure 10:
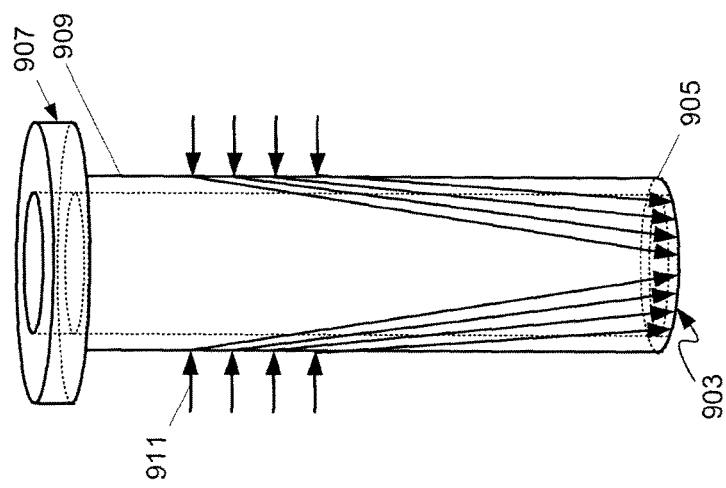

FIG. 10 the optical probe of FIG. 9 in operation, according to non-limiting implementations.

Figure 11:
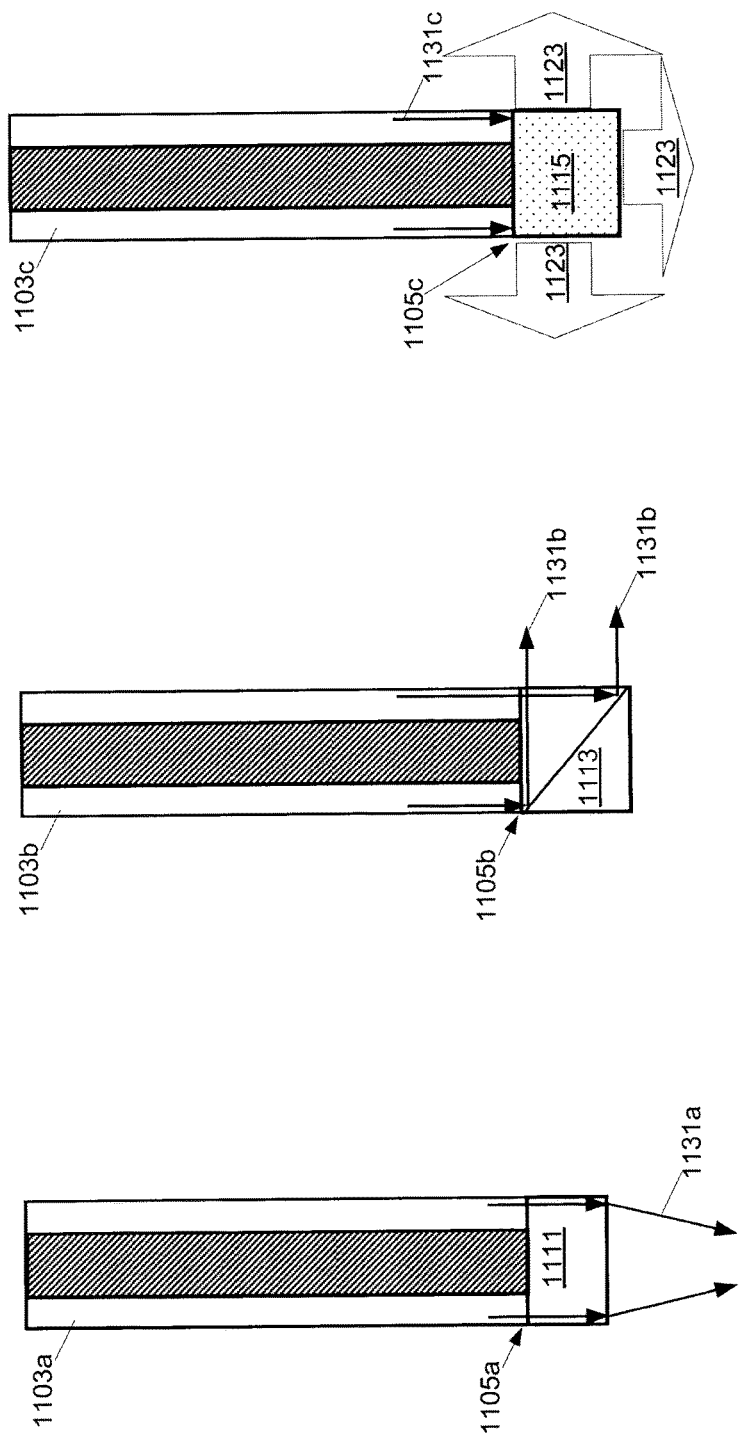

FIG. 11 depicts optical probes adapted to include an optical component at a distal end, according to non-limiting implementations.

Figure 12:
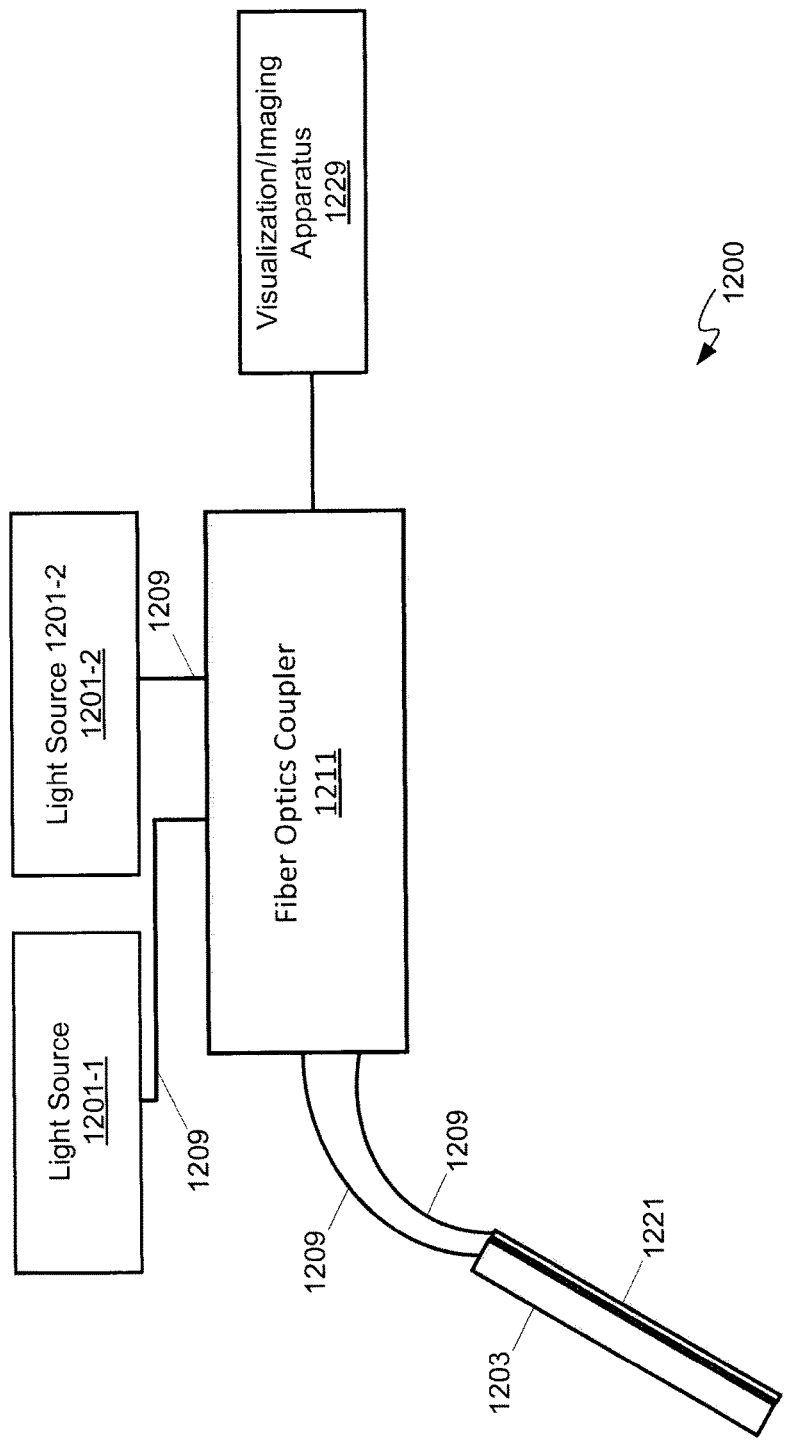

FIG. 12 depicts a system which includes an optical probe that conveys light to sample from two light sources, and a visualization and/or imaging apparatus, according to alternative non-limiting implementations.

Figure 13:
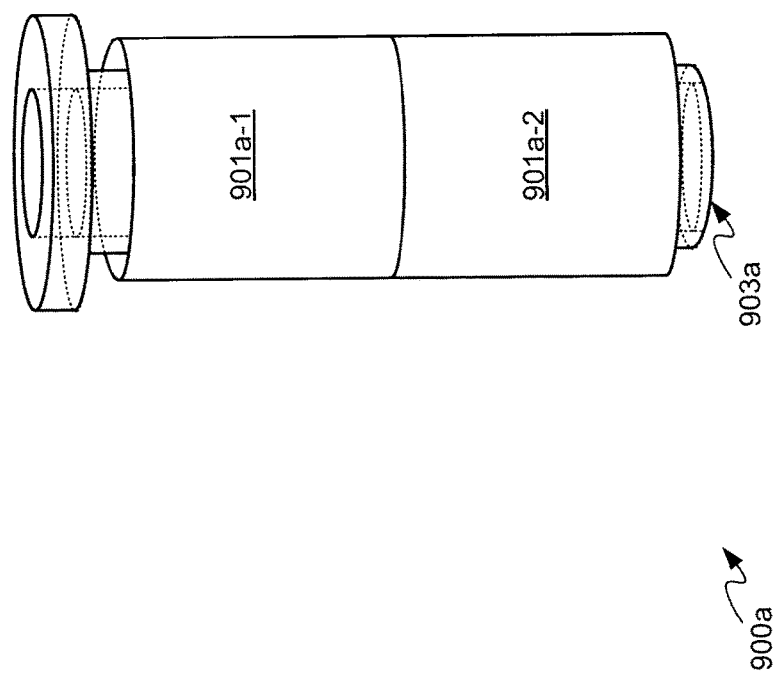

FIG. 13 depicts a system which includes an optical probe that conveys light to sample from a light source using sidewalls of the optical probe, according to alternative non-limiting implementations.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
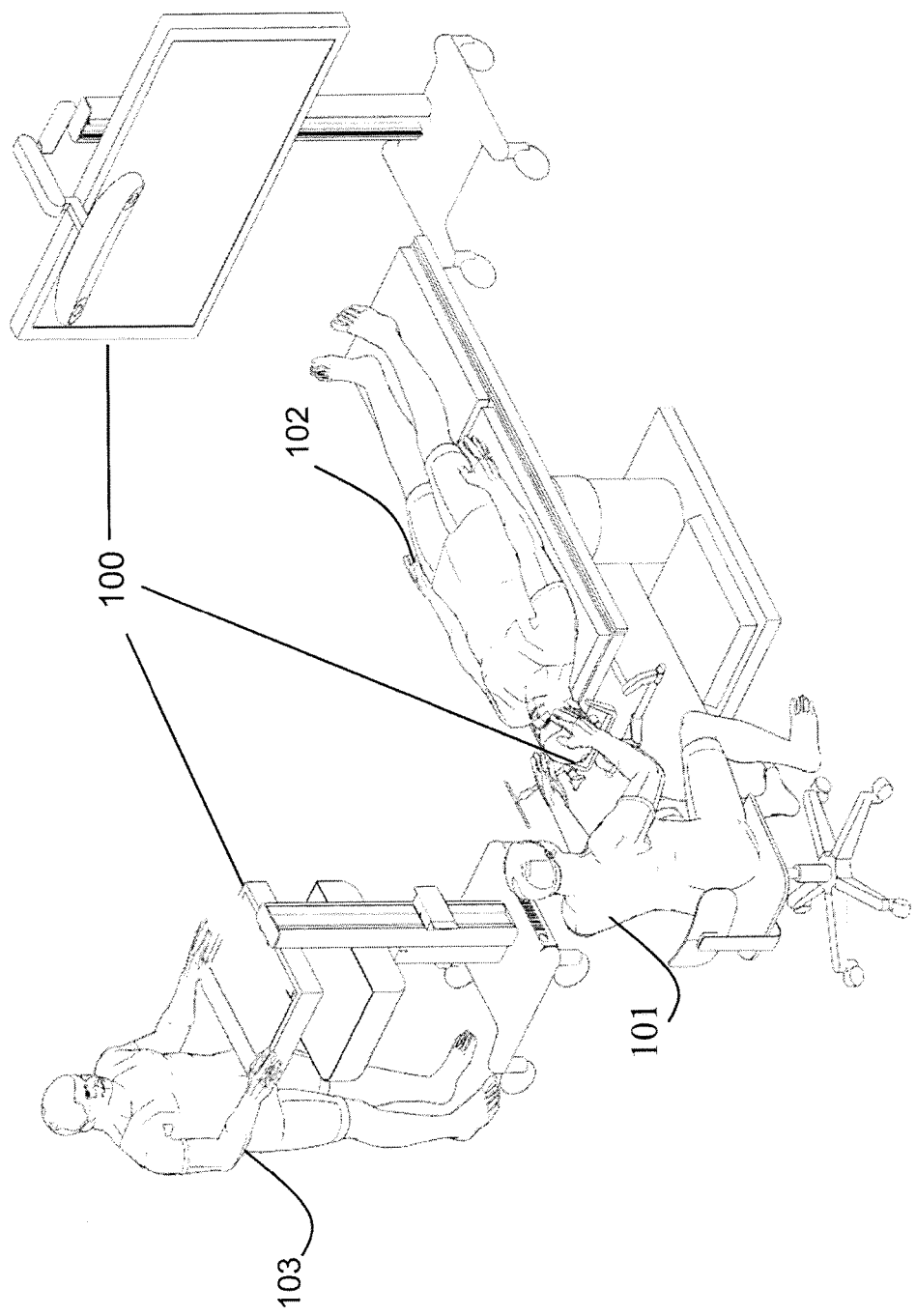
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
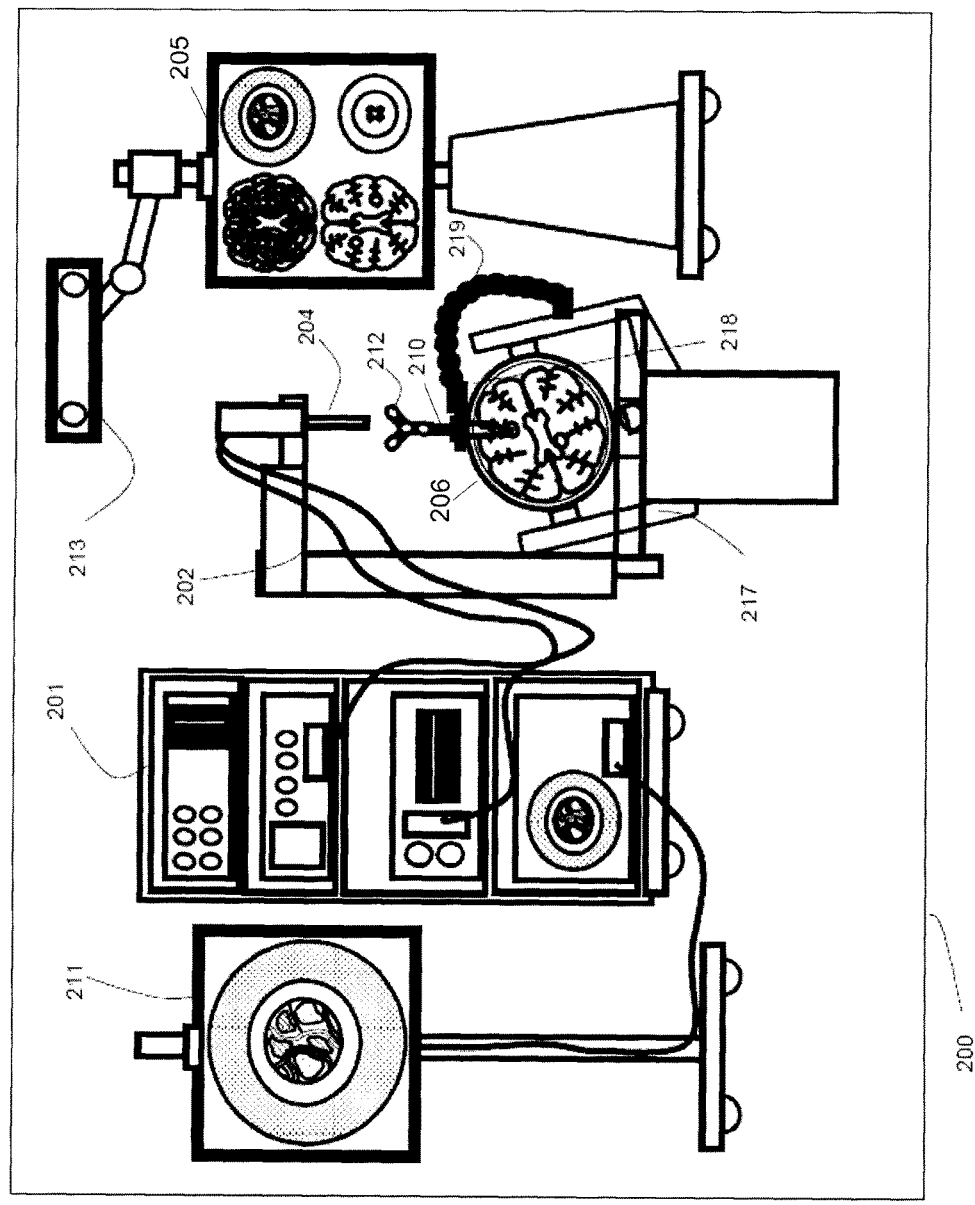
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
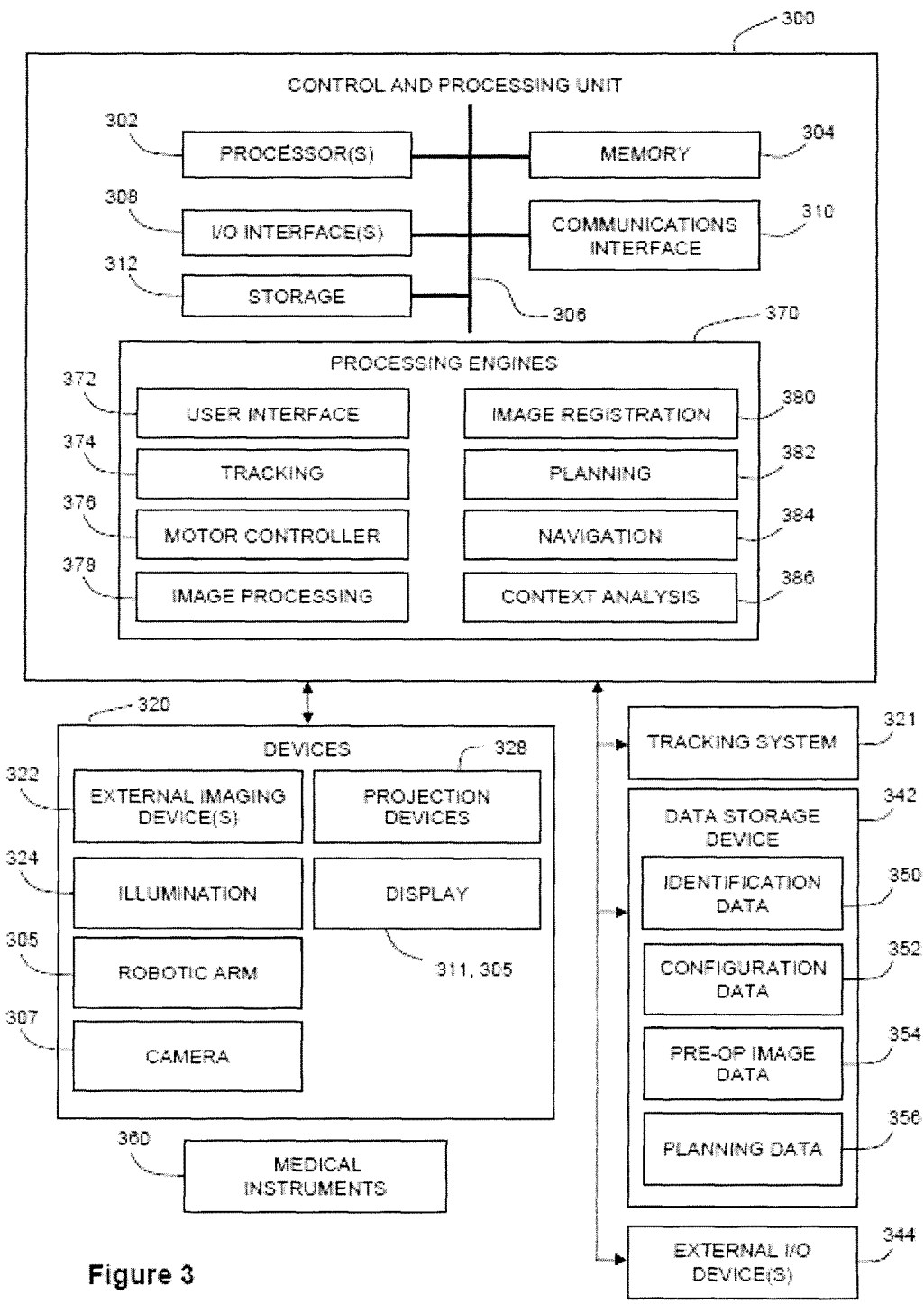
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
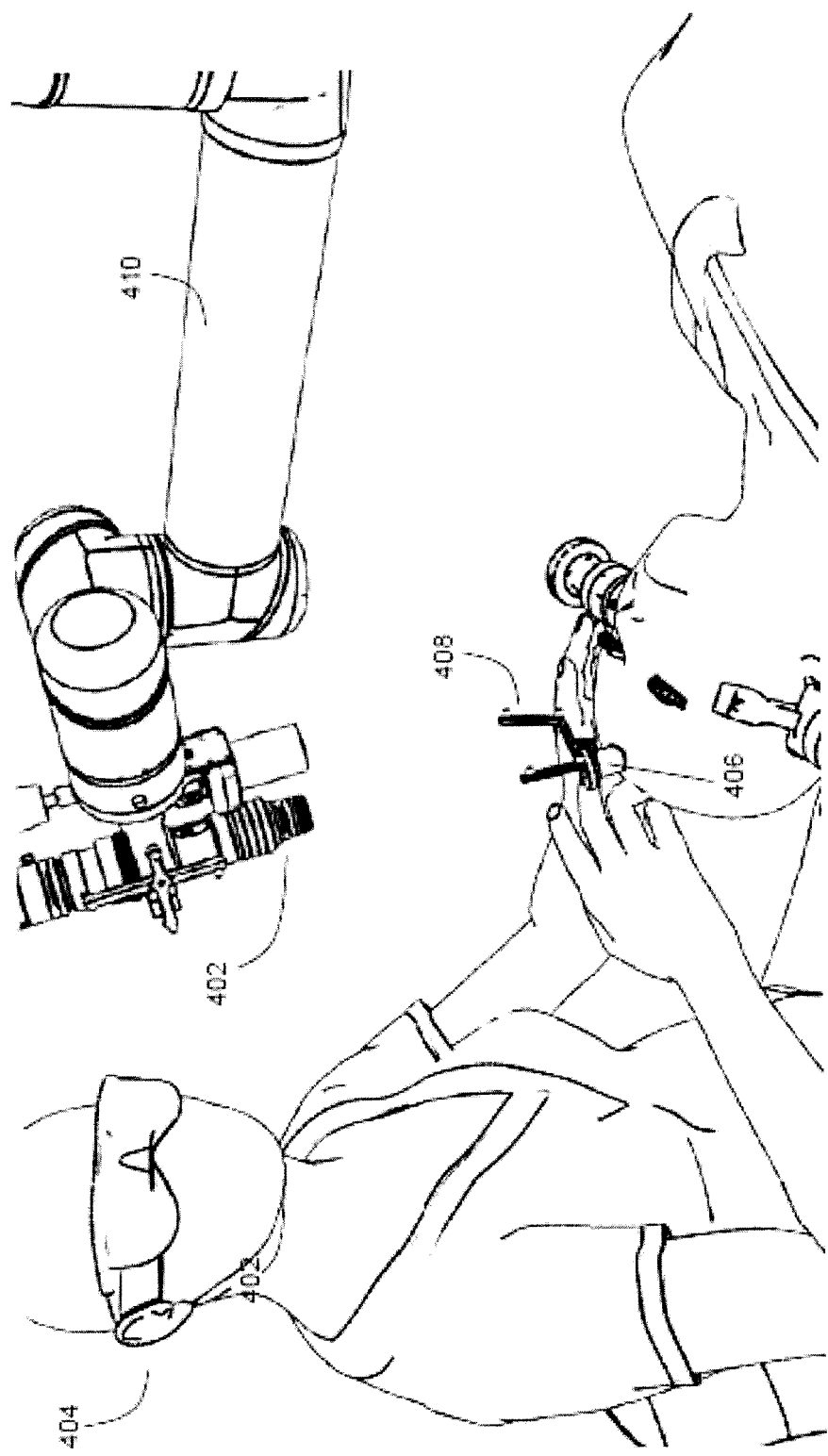
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
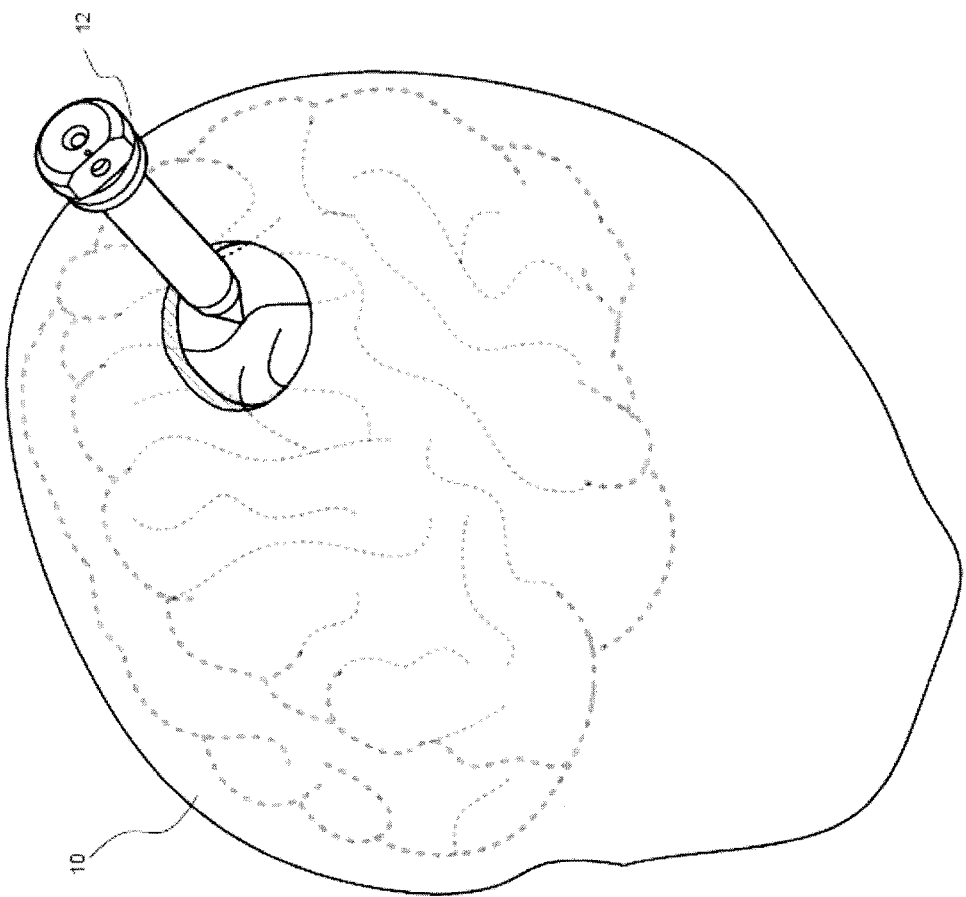
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments would then be inserted down the access port 12.

A further challenge of defining an appropriate access path is the concern of illumination. Illuminating the surgical field for port-based corridor surgeries is difficult as light must be driven down a narrow access port resulting in limited illumination. Further, non-uniform reflections may obfuscate the view of the desired target.

Hence, attention is next directed to FIG. 6, which depicts an optical port system 600 comprising: one or more light sources 601; and, an optical probe 603 comprising: a tube 604 having a distal end 605, a proximal end 607 and one or more sidewalls 609 there between, optical probe 603 and light source 601 arranged so that light 611 from light source 601 is received by one or more sidewalls 609, one or more sidewalls 609 configured to convey light 611 to distal end 605, distal end 605 configured to receive the light and illuminate a sample adjacent thereto. One or more sidewalls 609 will be interchangeably referred to hereafter as sidewalls 609; similarly, one or more light sources 601 will be interchangeably referred to hereafter as light source 601 (i.e. reference to sidewalls may include one sidewall, and reference to a light source may include more than one light source). Further, while only one ray of light is numbered in FIG. 6, it is appreciated that each arrow emitted from light source 601 represents light 611; this convention will be used throughout the remainder of the present specification.

The terms proximal end and distal end are used as, when optical probe 603 is in use, proximal end 607 will be proximal a surgeon, and the like, inserting surgical tools through tube 604, and distal end 605 will be distal the surgeon, and the like.

In other words, tube 604 generally comprises a port configured to receive at least one surgical instrument at proximal end 607 through to distal end 605, and distal end 605 may hence be further configured to illuminate an area of the sample with which the surgical instrument is interacting.

Light source 601 may be configured to emit one or more of: visible light, non-visible light, infrared light and ultraviolet light. In other words, system 600 may be adapted for optical modalities that include visible light, infrared light and/or ultraviolet light, as discussed in further detail below. However, as depicted, light source 601 may comprise any combination of light emitting device that emit in one or more defined wavelength ranges. For example, light source 601 may comprise any combination of light emitting diodes (LEDs), organic light emitting diodes (OLEDs), lasers, light bulbs, electroluminescent materials, and the like.

As depicted, light source 601 and optical probe 603 are arranged so that light 611 from light source 601 enters sidewalls 609 via proximal end 607. Indeed, as depicted, proximal end 607 comprises a rim 613 that has an outer diameter larger than an outer diameter of tube 604, rim 613 being optically coupled and/or integrated with sidewalls 609, so that light entering the rim from light source 601 is conveyed down side walls 609 to exit optical probe 603 at distal end 605. However, in other implementations proximal end 607 may be similar to distal end 605 and/or lacking rim 613.

As depicted, sidewalls 609 are substantially cylindrical. However, in other implementations, sidewalls 609 may have any profile whereby a surgical instrument is insertable through tube 604 so that a sample may be operated on via distal end 605. Hence, sidewalls 609 may be rectangular, square, octagonal, and the like, for example in transverse cross-section. Furthermore, an exterior of sidewalls 609 may have a same or different profile as an interior of sidewalls 609.

Furthermore, as depicted, at least sidewalls 609 may be substantially transparent between distal end 605 and proximal end 607, and/or comprise glass and/or comprise a transparent material. Interior walls of tube 604, for example, are drawn as stippled lines. Indeed, as depicted, rim 613 is also transparent.

Further, as depicted, at least sidewalls 609 comprise an integrated light guide; in other words, at least sidewalls are integrated with each of proximal end 607 and distal end 605, as well as rim 613, so that light 611 may travel through sidewalls 609, and/are reflected through sidewalls 609, without encountering an optical interface (other than the interface between proximal end 607 and an external medium, such as air, and between distal end 605 and an external medium, such as air, and/or any medium exterior to distal end 605).

This is further illustrated in FIG. 7, which depicts optical probe 603 receiving light 611 at proximal end 607, and conveying light 611 to distal end 605, and further depicts light 611 exiting distal end 605. In other words, light received through proximal end 607 travels through sidewalls 609 and exits distal end 605 to illuminate a sample adjacent distal end 605.

While in FIG. 7, light 611 is depicts as passing through sidewalls 609 in generally straight lines, it is appreciated that light 611 may follow curves and/or a shape of sidewalls 609. Furthermore, sidewalls 609 may be configured to assist in conveying light 611 to distal end 605. For example, in some implementations, system 600 may comprise one or more optical coatings on one or more sidewalls 609, the optical coatings configured to assist in conveying the light to distal end 605; in such implementations each of an interior side and an exterior side of sidewalls 609 may be coated with one or more optical coatings configured to reflect light in a range of wavelengths of light 611.

In other words, light source 601 may be configured to emit one or more of: visible light, non-visible light, infrared light and ultraviolet light, and any optical coatings on sidewalls 609 may be configured to reflect similar wavelengths of light emitted by light source 601 and/or configured to reflect wavelengths of light emitted by light source 601 that are in a given predefined range. For example, light source 601 may be configured to emit both infrared and visible light, but in some implementations only visible light may be of interest to a user of system 600; hence, the optical coatings may be configured to reflect visible light without concern for any reflectance of the infrared light.

Furthermore, as depicted, proximal end 607 receives light 611 and light 611 exits distal end 605. In some implementations, one or more of proximal end 607 and distal end 605 may comprise one or more anti-reflective optical coatings which are anti-reflective in a similar wavelength range as light 611, so that losses due to reflective interfaces are minimized.

In any event, while FIG. 7 depicts light 611 travelling through and/or along sidewalls 609, in other implementations, one or more sidewalls 609 may be configured to one or more of: mix light 611 when received therein; homogenize light 611 when received therein; and integrate light 611 when received therein. For example, sidewalls 609 may comprise material which diffuses and/or integrates and/or scatters light 611 rather than sidewalls 609 being merely transparent, so that light 611 existing distal end 605 has a relatively uniform profile.

Returning to FIG. 6, light source 601 is generally depicted as simply emitting light 611 towards proximal end 607. While in such implementations, light source 601 is in optical communication with proximal end 607, and proximal end 607 is generally configured to receive light 611 from light source 601, in implementing system 600 in surgery, system 600 may further comprise a light guide between an output of light source 601 and proximal end 607, to assist in the optical communication there between, as simply aiming light 611 from light source 601 towards proximal end 607 (as depicted) may not be practical. For example, system 600 may further comprise one or more optical fibers (not depicted, however see FIG. 12) configured to convey light 611 from light source 601 to one or more of proximal end 607 and one or more sidewalls 609.

In yet further implementations, light source 601 may be adapted to more directly optically interact with proximal end 607. For example, attention is next directed to FIG. 8, which depicts a system 800 that comprise optical probe 603, and a light source 801 located at proximal end 607 of optical probe 603, light source 801 configured to emit light 811 in a similar configuration to rim 813. For example, light source 801 comprises a ring having an aperture and/or an inner diameter similar to an inner diameter of tube 604, and an outer diameter that may be the same or different from an outer diameter of proximal end 607 (and/or of rim 613), and light source 801 emits light 811 along the ring. In particular, light source 801 may comprise one or more an electroluminescent material, an electroluminescent sheet, a organic light emitting diode (OLED) matrix, and an OLED sheet, and light emitting diodes (LEDs), arranged around the aperture on a side of ring facing proximal end 607. The aperture of light source 801 is configured to allow surgical instruments to pass therethrough.

While not depicted, it is assumed that system 800 further comprises: a power source; and an electrical connection between the power source and light source 801, in order to power light source 801. Similar assumptions are made regarding other light sources described heretofore and hereafter.

While each of systems 600 and 900 depict different implementations where light is received in sidewalls 609 at distal end 605, in other implementations, sidewalls 609 may be adapted to receive light from a light source through an exterior side and/or an interior side of sidewalls 609. For example, attention is next directed to FIG. 9, which is similar to FIG. 6, with like elements having like numbers, but preceded by a "9" rather than a "6". Specifically, FIG. 9 depicts a system 900 comprising: a light source 901; and, an optical probe 903 comprising: a tube 904 having a distal end 905, a proximal end 907 and one or more sidewalls 909 there between, optical probe 903 and light source 901 arranged so that light from light source 901 is received by one or more sidewalls 909, one or more sidewalls 909 configured to convey the light to distal end 905, distal end 905 configured to receive the light and illuminate a sample adjacent thereto.

As depicted, light source 901 comprises a light emitting sheet that at least partially wraps around sidewalls 909; light source 901 may be in contact with an exterior side of sidewalls 909 and/or spaced there from. For example, light source 901 may comprise one or more of an electroluminescent material, an electroluminescent sheet, a organic light emitting diode (OLED) matrix, and an OLED sheet, and the like which at least partially wraps around sidewalls 909. Furthermore light source 901 is configured to emit light towards an external side of sidewalls 909. Hence, in these implementations, an external side of one or more sidewalls 909 is generally transparent and light source 901 is located at the external side of one or more sidewalls 909.

In particular non-limiting implementations, light source 601 may include an OLED substrate sheet comprising a plurality of OLEDs embedded throughout the sheet where light emitted there from is reflected through sidewalls 909 to distal end 905.

Light source 901 may be flexible or non-flexible. For example, in some implementations, light source 901 may comprise light emitting films deposited onto an exterior side of sidewalls 909 using vacuum techniques, sol-gel techniques, and the like. Alternatively, light source 901 may comprise a flexible light emitting material that may be formed separately from optical probe 903 and at least partially wrapped around an exterior side of sidewalls 909.

Furthermore, in these implementations, where an external side of one or more sidewalls 909 is generally transparent, light source 901 is proximal the external side of one or more sidewalls 909, the external side of sidewalls 909 may comprise one or more optical coatings configured to convey light from light source 901 into one or more sidewalls 909 (e.g. exterior optical coatings may comprise an antireflective coating), and an interior side of one or more sidewalls 909 may be configured to one or more of: reflect the light back into one or more sidewalls 909, and direct light towards distal end 905. For example, an interior side of sidewalls 909 may comprise optical coatings, optical treatments, optical devices, and the like configured to one or more of: reflect the light back into one or more sidewalls 909 and direct light towards distal end 905. For example, an interior side of sidewalls 909 may comprise one or more GRIN (gradient index) optics devices configured to receive light through an exterior side of sidewalls 909 and direct the light towards distal end 905.

Operation of optical probe 903 is depicted in FIG. 10; while light source 901 is not depicted for clarity, it is assumed that light source 901 is located at a same position relative to optical probe 903 as in FIG. 9, and further that light source 901 is emitting light 911 towards sidewalls 909. While light 911 is depicted as being generally parallel for convenience, light source 901 may comprise a Lambertian light source (e.g. its brightness appears about the same from any angle of view), a diffuse light source, a Gaussian light source and the like. Indeed, any suitable light profile of light source 901 is within the scope of present implementations. In some implementations, a light emitting side of light source 901 may be configured to direct light into sidewalls 909 and towards distal end 905; for example a light emitting side of light source 901 may comprise GRIN optics and the like that receives emitted light and bends the light into sidewalls 909 towards distal end 905.

In any event, light 911 is received through an exterior side of sidewalls 909 and, as depicted, is guided through sidewalls 909 by any suitable technique, including optical coatings and/or optical devices at an interior side of sidewalls 909. Indeed, in these implementations, proximal end 907 may include reflective coatings to reflect light reflected there to back towards distal end 905. Further, as with optical probe 603, sidewalls 909 may comprise a light guide. Further, sidewalls 909 may be configured to one or more mix light 911 when received therein; homogenize light 911 when received therein; and integrate light 911 when received therein.

Further, light received through sidewalls 909 is conveyed to distal end 905 to illuminate a sample adjacent thereto, similar to other optical probes described herein.

While not depicted, in yet further implementations, a light source similar to light source 901 may be located adjacent inside tube 904 and/or adjacent an interior side of sidewalls 909, with the interior side of sidewalls 909 configured to receive light into sidewalls 909, and an exterior side of sidewalls 909 configured to one or more of: reflect the light back into one or more sidewalls 909 and direct light towards distal end 905.

In yet further implementations, a first light source similar to light source 901 may be located adjacent an exterior side of sidewalls 909, and a second light source similar to light source 901 may be located inside tube 904 and/or adjacent an interior side of sidewalls 909.

In yet further implementations, aspects of each of optical probes 603, 903 may be combined. For example, an optical probe as disclosed herein may be configured to receive light through an exterior side and/or an interior side of sidewalls, and through a proximal end.

In some implementations, light source 901 may comprise two or more light sources of different modalities. For example, attention is directed to FIG. 13 which depicts a system 900a which is substantially similar to system 900 with like elements having like numbers, with an "a" appended thereto. Hence system 900a comprises two light sources 901a-1, 901a-2 (interchangeably referred to hereafter, collectively, as light sources 901a and generically as a light source 901a), and an optical probe 903a. Each of light sources 901a comprise a light source of different optical modality, but is otherwise similar to light source 901; however, each light source 901a is wrapped around different portions of sidewalls of optical probe 903a. For example, light source 901a-1 may be configured to emit light in an infrared range of wavelengths, while light source 901a-2 may be configured to emit light in a visible (to humans) range of wavelengths. While each light source 901a is located along a different portion of optical probe 903a, light from each is conveyed by optical probe 903a to a distal end thereof, as described above.

Respective power connections thereto may be used to turn on and turn off each light source 901a independent of each other. Intensities of each light source 901a may be controlled and/or independently controlled to provide different illumination intensities of a sample adjacent the distal end of optical probe 903a.

Furthermore, while light source 901a-1 is depicted as being located towards a proximal end of optical probe 903a, and light source 901a-2 is depicted as being located towards a distal end of optical probe 903a, and further while light sources 901a are depicted adjacent to each other and covering about a same area, in other implementations, respective locations, and respective areas of each light source 901a may be varied and/or adapted for particular situations. For example, respective areas of each light source 901a may be changed to increase or decrease respective intensities of each.

Returning to FIGS. 9 and 10, in some implementations, light source 901 may comprise one or more of a matrix of light sources, an array of light sources, and the like. For example, light source 901 may comprise a plurality of pixels that are addressable using a connection (not depicted) to a control system, such as the system depicted in FIG. 3. For example, each pixel may comprise one or more LEDs, one or more OLEDs and the like. As such, in these implementations, each pixel may be turned on and off independent of the other pixels and further an intensity and/or brightness of each pixel may be controlled independent of the other pixels (e.g. using PWM (Pulse Width Modulation) and the like. As such, in these implementations, light source 901 may be controlled to shape illumination at distal end 905 to counteract non-uniform lighting and/or shadowing caused by surgical tools inserted through tube 904. Furthermore, when light source 901 comprises such an addressable matrix and/or addressable array, and a navigation system is being used to track navigation of surgical tools through tube 904, one or more of a navigated pose and/or a navigated position of the surgical tools down tube 904 may be used to shape the illumination to account for the surgical tool's shadows, reflections, etc. In other words, a position and/pose of the surgical tool may be determined using a navigation system (such as tracking system 321 of FIG. 3) and light source 901 may be controlled according to one or more of a position and a pose of the surgical tool; it is assumed in these implementations that the navigation system is in communication with a control system configured to control the addressable matrix and/or the addressable array of light sources of light source 901. In other words tracking and/or navigation of surgical tools, and responsive controlling of light source 901, may be used in combination with selectively illumination regions of a surgical field based on a context of the surgery. For example a software control and navigation system may be used to assess the location of a resection tool, an array of light sources at light source 901 may selectively activated to avoid creation of shadows and/or to minimize occlusion of a surgical field by shadows cast by the surgical tools themselves. In particular, one or more of an external side and an internal side of one or more sidewalls 909 can be generally transparent and one or more light sources 901 can be located at one or more of the external side and the internal side of one or more sidewalls 909, one or more light sources 901 comprising an addressable matrix of pixels in communication with a control system. The control system can be in communication with a navigation system configured to track one or more of a position and a pose of at least one surgical instrument used with optical probe 903, the control system configured to control the addressable matrix of pixels in response to one or more of the position and the pose of the at least one surgical instrument.

In some implementations, a distal end of optical probes disclosed herein may be adapted to focus and/or direct light in a given direction and/or towards a sample. For example, attention is next directed to FIG. 11, which depicts three implementations of optical probe 1103a, 1103b, 1103b, where respective corresponding distal ends 1105a, 1105b, 1105c have been adapted to include, respectively, a light focusing device 1111, a mirror 1113 and a light diffusing device 1115. It is further appreciated that each of optical probe 1103a, 1103b, 1103b are depicted schematically, but each may be similar to optical probe 603 and/or optical probe 903 as described above.

Light focusing device 1111 may comprise one or more of a lens, a faceted lens, a microlens, gradient index (GRIN) optics and the like; light focusing device 1111 is generally configured to receive light 1131a (e.g. from a light source as described above, and through sidewalls of optical probe 1103a) and focus light 1131a in a given direction, for example, and as depicted, along a longitudinal axis of optical probe 1103a, however light focusing device 1111 may be configured to focus light 1131a in any suitable direction.

Mirror 1113 may comprise one suitable mirror including, but not limited to, one or more of a metallic coated glass mirror, a dichroic mirror, and the like. Mirror 1113 is generally configured to receive light 1131b (e.g. from a light source as described above, and through sidewalls of optical probe 1103b) and reflect light 1131b in a given direction, for example, and as depicted, about perpendicular to a longitudinal axis of optical probe 1103b. However light mirror 1113 may be configured to reflect light 1131b in any suitable direction.

Light diffusing device 1115 may comprise any suitable light diffuser, including, but not limited to, a film-based diffuser, frosted glass, a polymer based diffuser, and the like. Light diffusing device 1115 is generally configured to receive light 1131c (e.g. from a light source as described above, and through sidewalls of optical probe 1103c) and diffuse light 1131c. In some implementations, light diffusing device 1115 may be configured to diffuse light 1131c in one or more given directions, for example, and as depicted, along a longitudinal axis of optical probe 1103c, and about perpendicular to the longitudinal axis of optical probe 1103c; diffused light is referred to in FIG. 11 as diffused light 1123. However light diffusing device 1115 may be configured to diffuse light 1131c in any suitable direction.

In yet further implementations, light focusing devices, mirrors, and light diffusing devices may be combined, for example to one or more of focus light, reflect light and diffuse light in one or more given directions. Furthermore, such optical components located at a distal end of optical probes described herein may be modular, and furthermore a distal end of optical probes described herein may be adapted for attachment to such optical components. In alternative implementations, a respective distal end of each optical probe 1103a, 1103b, 1103c may have optical components as described herein built in the port 60 to direct respective light accordingly.

Furthermore, any optical components located at a distal end of optical probes disclosed herein are configured to not interfere with surgical instruments inserted through a tube of the optical probes. Hence, such optical components may comprise suitable apertures, gaps, and the like, for at least an end of surgical instruments to pass there through.

Attention is next directed to FIG. 12, which depicts a system 1200 comprising: one or more light sources 1201-1, 1201-2 (interchangeably referred to hereafter, collectively, as light sources 1201 and generically as a light source 1201) configured to provide light to an optical probe 1203, which is similar to one or more of optical probes 603, 903, 1103a, 1103b, 1103c, via combinations of optical fibers 1209, and via an optical coupler 1211. Each of light sources 1201 may comprise light sources of different optical modalities; for example, light source 1201-1 may comprise a fluorescence light source, while light source 1201-2 may comprise a laser light source. Alternatively, system 1200 may comprise light sources similar to light source 901 that at least partially wrap around sidewalls of optical probe 1203 similar to light sources 901a in FIG. 13.

In other words, in general, optical probe 1203 is configured to convey light to a sample adjacent a distal end thereof.

System 1200 further comprises light collection apparatus 1221 configured to collect light reflected from a sample adjacent a distal end of optical probe 1203, and a one or more of optical visualization apparatus and imaging apparatus 1229, configured to communicate with light collection apparatus 1221 to image the sample from the light reflected from the sample, using one or more of visible light, non-visible light, infrared light and ultraviolet light. In other words one or more of light sources 1201 may emit one or more of visible light, non-visible light, infrared light and ultraviolet light which is conveyed to a sample by optical probe 1203, and reflected light is collected by light collection apparatus 1221, which is conveyed to apparatus 1229 using one or more optical fibers 1209 and fiber optics coupler 1211 (i.e. it is assumed in FIG. 12 that fiber optics coupler 1211 is configured to convey light from and to various components using optical fibers 1209). In other implementations, however the light sources 1201 may be configured similar to light sources 901a depicted in FIG. 13.

Light collection apparatus 1221 may comprise optical fibers, light guides and the like configured to collect light reflected from a sample illuminated using optical probe 1203. While light collection apparatus 1221 is depicted as being located external to optical probe 1203, in other implementations, light collection apparatus 1221 may be located internal to optical probe 1203 (e.g. inside a tube of optical probe 1203). Alternatively, light collection apparatus 1221 may be incorporated into sidewalls of optical probe 1203; in other words, in these implementations, sidewalls of optical probe 1203 are configured to both convey light from light sources 1201 to a sample adjacent a distal end of optical probe 1203, and collect light reflected from the sample, as well as convey reflected light back to an optical fiber 1209 connected thereto, and/or to apparatus 1229.

Apparatus 1229 may comprise any suitable optical visualization apparatus and/or imaging apparatus, including, but not limited to, a camera, a display and the like, as well as suitable light analysis devices. Apparatus 1229 may further be configured for compatibility with wavelengths of light of light sources 1201; in other words, when light sources 1201 emit infrared light, apparatus 1229 may be configured to image infrared light.

Described herein are systems that include one or more light sources and an optical probe that is configured to convey light from the one or more light sources through sidewalls thereof to a distal end where the light exits and illuminates a sample adjacent thereto.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An optical port system for a corridor based procedure comprising: one or more light sources; and, an optical probe comprising: a tube having a distal end, a proximal end and one or more sidewalls there between, the optical probe and the one or more light sources arranged so that light from the one or more light sources is received by the one or more sidewalls, the one or more sidewalls configured to convey the light to the distal end, the distal end configured to receive the light and illuminate a sample adjacent thereto, further comprising light collection apparatus configured to collect the light reflected from the sample, and a one or more of optical visualization apparatus and imaging apparatus, configured to communicate with the light collection apparatus to image the sample from the light reflected from the sample, using one or more of visible light, non-visible light, infrared light and ultraviolet light.

2. The optical port system of claim 1, wherein the one or more sidewalls are substantially cylindrical.

3. The optical port system of claim 1, wherein the one or more sidewalls are further configured to one or more of: mix the light when received therein; homogenize the light when received therein; and integrate the light when received therein.

4. The optical port system of claim 1, wherein the one or more sidewalls comprise an integrated light guide.

5. The optical port system of claim 1, wherein the one or more sidewalls are generally transparent between the distal end and the proximal end.

6. The optical port system of claim 1, wherein the one or more light sources is in optical communication with the proximal end, the proximal end configured to receive the light from the one or more light sources.

7. The optical port system of claim 1, further comprising one or more optical fibers configured to convey the light from the one or more light sources to one or more of the proximal end and the one or more sidewalls.

8. The optical port system of claim 1, wherein the distal end comprises one or more of: a lens, a microlens, a mirror, a light focusing device, and a light diffusing device.

9. The optical port system of claim 1, wherein the one or more sidewalls comprise glass.

10. The optical port system of claim 1, wherein an external side of the one or more sidewalls is generally transparent and the one or more light sources is located at the external side of the one or more sidewalls.

11. The optical port system of claim 1, wherein an internal side of the one or more sidewalls is generally transparent and the one or more light sources is located at the internal side of the one or more sidewalls.

12. The optical port system of claim 1, wherein one or more of an external side and an internal side of the one or more sidewalls is generally transparent and the one or more light sources is located at one or more of the external side and the internal side of the one or more sidewalls, the one or more light sources comprising one or more of an electroluminescent material, an electroluminescent sheet, a organic light emitting diode (OLED) matrix, and an OLED sheet.

13. The optical port system of claim 1, further comprising a control system, and wherein one or more of an external side and an internal side of the one or more sidewalls is generally transparent and the one or more light sources is located at one or more of the external side and the internal side of the one or more sidewalls, the one or more light sources comprising an addressable matrix of pixels in communication with the control system.

14. The optical port system of claim 1, wherein the control system is in communication with a navigation system configured to track one or more of a position and a pose of at least one surgical instrument used with the optical probe, the control system configured to control the addressable matrix of pixels in response to one or more of the position and the pose of the at least one surgical instrument.

15. The optical port system of claim 1, wherein one or more of an external side and an internal side of the one or more sidewalls is generally transparent and the one or more light sources comprises a flexible light emitting material located at one or more of the external side and the internal side of the one or more sidewalls.

16. The optical port system of claim 1, wherein an external side of the one or more sidewalls is generally transparent and the one or more light sources is proximal the external side of the one or more sidewalls, the external side comprising one or more optical coatings configured to convey light from the one or more light sources into the one or more sidewalls, and an interior side of the one or more sidewalls configured to reflect the light back into the one or more sidewalls.

17. The optical port system of claim 1, further comprising one or more optical coatings on the one or more sidewalls, the optical coatings configured to assist in conveying the light to the distal end.

18. The optical port system of claim 1, further comprising: a power source; and an electrical connection between the power source and light source.

19. The optical port system of claim 1, wherein the one or more light sources is configured to emit one or more of: visible light, non-visible light, infrared light and ultraviolet light.

20. The optical port system of claim 1, wherein the tube comprises a port configured to receive at least one surgical instrument at the proximal end through to the distal end, and the distal end is further configured to illuminate an area of the sample with which the surgical instrument is interacting.

* * * * *